United States Patent [19]

Katsura et al.

[11] Patent Number: 4,622,032
[45] Date of Patent: Nov. 11, 1986

[54] BLOOD RESERVOIR

[75] Inventors: Yoshiro Katsura, Fuji; Kazuhiko Hagiwara; Osamu Nomura, both of Fujinomiya, all of Japan

[73] Assignee: Terumo Kabushiki Kaisha, Tokyo, Japan

[21] Appl. No.: 791,568

[22] Filed: Oct. 25, 1985

[30] Foreign Application Priority Data

Oct. 27, 1984 [JP] Japan ................................ 59-226584

[51] Int. Cl.⁴ ...................... A61M 1/03; B01D 19/02
[52] U.S. Cl. ...................................... 604/122; 604/4; 604/408
[58] Field of Search .............................. 604/4–6, 604/122, 251, 408; 128/DIG. 3; 422/44–48

[56] References Cited

U.S. PATENT DOCUMENTS

| 3,911,918 | 10/1975 | Turner | 422/44 |
| 4,026,669 | 5/1977 | Leonard | 422/44 |
| 4,428,743 | 1/1984 | Heck | 604/122 |
| 4,493,705 | 1/1985 | Gordon et al. | 604/122 |
| 4,568,330 | 2/1986 | Kujawski et al. | 604/4 |

Primary Examiner—Dalton L. Truluck
Assistant Examiner—Michelle N. Lester
Attorney, Agent, or Firm—Burns, Doane, Swecker & Mathis

[57] ABSTRACT

In a blood reservoir comprising a hollow rectangular container for containing blood therein, a projected portion is provided on one vertical side of the container that is remoter from blood inlet means and nearer to blood outlet means by projecting into the container space substantially from the intersection between the one side and a horizontal extension of the blood inlet.

5 Claims, 7 Drawing Figures

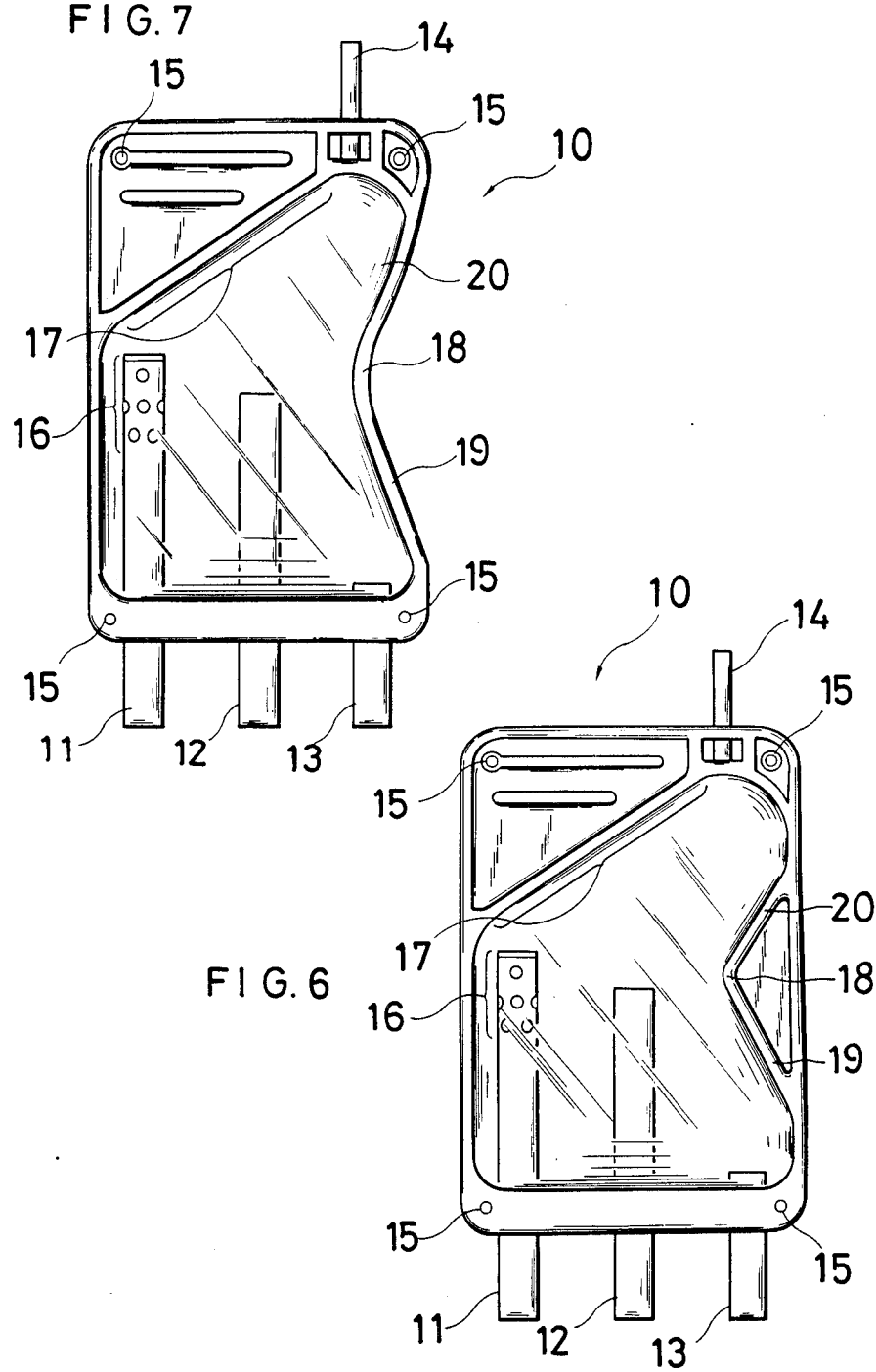

BLOOD RESERVOIR

BACKGROUND OF THE INVENTION

This invention relates to a blood reservoir in a closed oxygenator circuit for temporarily collecting venous blood drained from a patient, and more particularly, to a small-sized venous blood reservoir intended for use in an oxygenator circuit for a neonate or infant.

Conventional venous blood reservoirs of closed type are designed (1) to have a sufficient volume to contain a predetermined volume of blood in order to provide a blood collecting function, (2) to control the blood collecting space or blood flow so as to remove air mixed in the drained blood, and (3) to prevent local blood stagnation within the reservoir.

To achieve air removal from the drained blood, the blood reservoir should have a space of dimensions sufficient for collecting blood therein. Differently stated, a room for blood stagnation should intentionally be provided. This is contrary to the above-mentioned requirement (3). More difficulty arises in manufacturing a flood reservoir of a smaller volume.

In order to overcome these difficulties, attempts have been made to remove air from the drained blood by controlling the blood flow in the blood collecting space. One such technique is to form a plurality of blood inlet openings around the top end of the blood inlet tubing through which blood enters the reservoir as a diffused gentle stream, thereby allowing air bubbles to come up by F buoyancy as disclosed in U.S. Ser. No. 439,422 (European Pat. No. 80610). Another technique is to provide an area for blood stagnation between the blood inlet and outlet of the reservoir.

A venous blood reservoir for an oxygenator ciruclt of the type to be used for a neonate or infant requires an undesirably increased volume of priming blood unless it is made smaller in size than that for an adult.

Such a small-sized venous reservoir is very difficult to successfully remove air from the drained blood and to achieve debubbling by the conventional debubbling process employed in adult blood reservoirs.

In addition, when the blood reservoir of this type is bulged with blood, the reservoir made of a flexible vinyl chloride resin tends to give way at the intermediate thereof. Air bubbles collect and cling to the inside wall of the waisted portion and such clinging bubbles are difficult to remove therefrom. There is the need for an improved reservoir capable of preventing formation of such a waisted portion.

SUMMARY OF THE INVENTION

It is an object of the present invention to provide a closed system venous blood reservoir of a small volume capable of removing air efficiently from the drained blood.

Another object of the present invention is to provide such a venous blood reservoir which is prevented from forming a waisted portion even when the reservoir is bulged with blood, and thus free of blood stagnation below the waisted portion.

According to the present invention, there is provided a blood reservoir comprising:

a hollow container of a flexible synthetic resin defining a space for containing blood therein, vent means provided at an upper portion of said container in communication with the space of said container for venting air therefrom, and blood inlet means and blood outlet means each communicating with the space of said container, said blood inlet means including a tubular member extending into the space through a lower portion of said container and having a closed top end and a plurality of blood inlet openings perforated in a region of the wall of said tubular member extending downward from said closed top end, and said blood outlet means being located near the lower portion of the space for discharging blood therefrom, characterized in that a projected portion is provided on one side of an inner surface of said container that is remoter from said blood inlet means and nearer to said blood outlet means, said projected portion is projected into the container space from the vicinity of the intersection between said one side and a horizontal extension of said blood inlet means.

In one preferred embodiment of the present invention, said projected portion is formed entirely of said one side of said inner surface of said container nearer to said blood outlet means by projecting the side into the container space, said projected portion having a crest located in the vicinity of the intersection between said one side of said inner surface of said container and the horizontal extension of said blood inlet means.

More preferably, said one side of said inner surface of said container nearer to said blood outlet means consists of a section from said crest to the top of said space and a section from said crest to the bottom of said space, each section being substantially of a straight line for defining said projected portion.

In a further preferred embodiment of the present invention, the distance A between the top and the bottom of said space and the distance a between said crest and the bottom of said space have a relation:

$$0.2 \leq a/A \leq 0.8$$

Also preferably, said container is formed by sealing the side edges of a pair of synthetic resin sheets, said projected portion is provided at the one side of the inner surface of said sealed container, and said tubular member having said plurality of blood inlet openings is provided adjacent the other side of said container.

BRIEF DESCRIPTION OF THE DRAWINGS

FIGS. 6 and 7 are elevations showing blood reservoirs according to different embodiments of the present invention.

DESCRIPTION OF THE PREFERRED EMBODIMENTS

Figures 1, 3:
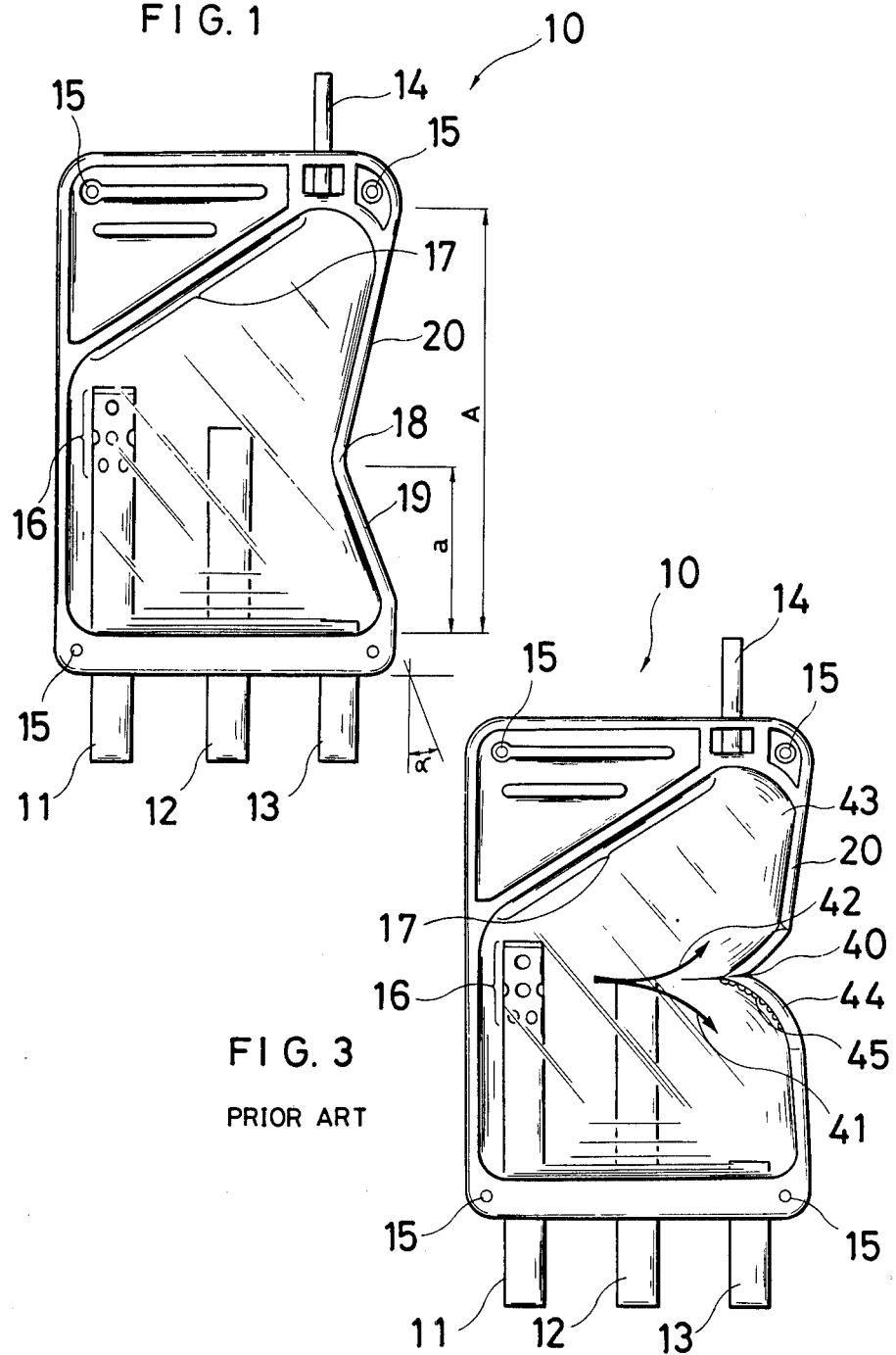
FIG. 1 is an elevation of a blood reservoir according to one preferred embodiment of the present invention.
FIG. 3 is an elevation of a conventional reservoir, illustrating blood streams across the waisted portion in the reservoir.

Referring to FIG. 1, there is illustrated one preferred embodiment of the blood reservoir of the present invention. A blood reservoir generally designated at 10 is a container formed of a synthetic resin. Such a container may preferably be formed by joining the edges of a pair of synthetic resin sheets, most preferably by sealing flexible polyvinyl chloride sheets with the application of high-frequency waves, whereby defining a space for receiving and collecting blood therein.

The blood reservoir of this invention comprises a container formed by sealing the side edges of paired plastic sheets preferably of a rectangular shape. The container thus formed is generally of a rectangular contour having two pairs of opposite sealed side edges. For convenience of description, the reservoir or container is explained as standing upright in FIG. 1 because it is held upright during its service. The reservoir is then described as having a pair of horizontal upper and lower side edges and a pair of vertical left and right side edges.

The reservoir 10 is provided with a blood inlet tubing 11 for introducing the blood drained from the patient and a cardiotomy line tubing 12 for passing the blood flowing out of a cardiotomy reservoir. Both tubings 11 and 12 extend through the lower portion of the reservoir 10 into the blood collecting space. The reservoir 10 is also provided with a blood outlet tubing 13 for discharging debubbled blood out of the reservoir 10. As shown in the figures, the inlet tubing 11 is located adjacent and parallel to the left vertical side, the cardiotomy line tubing 12 located intermediate, and the outlet tubing 13 located adjacent the right vertical side, all tubings extending through the lower sealed edge. Further, a vent line tubing 14 is provided in the upper side edge of the reservoir for exhausting the air resulting from debubbling of the collected blood in the reservoir 10.

The reservoir 10 is provided at its upper sealed portion with holes 15 for supporting the reservoir 10 onto a suitable holder during the service of the reservoir 10.

The blood inlet tubing 11 is closed at the top end thereof, and a plurality of ports or openings 16 perforated in a region of the wall of the blood inlet tubing 11, the region of the openings 16 extending downward from the closed top end. These openings 16 serve to conduct the blood as a gentle and quiet stream in a horizontal direction within the space of the container. If the openings 16 are located in an area around the bottom of the reservoir 10, the blood flowing out of the openings 16 immediately passes to the blood outlet tubing 13 without room for allowing bubbles to escape from the blood. Therefore it is necessary that the length of tubing 13 extending into the blood collecting space be not too short, and that the region where the openings 16 are provided in the tubing 11 be not too low.

The reservoir 10 includes an inclined portion 17 defining a part of the blood collecting space for ensuring that air bubbles floating and collecting around the inclined portion 17 move to the vent line tube 14.

The feature of the present invention resides in a projected portion 18 formed on one side, right side in FIG. 1, of an inner surface of the reservoir 10 which is remoter from the blood inlet tubing 11 and nearer to the blood outlet tubing 13. The projected portion is projected into the container space from the vicinity of the intersection between the one side of the reservoir 10 and a horizontal extension of the region of openings 16 of the blood inlet tubing 11.

One reason for forming a projected portion by projecting the one side of inner surface of the reservoir into its space is, in a negative sense, to avoid formation of a waisted portion on the side of the reservoir. As already mentioned in the preamble, when a rectangular reservoir as in this invention is bulged with blood, the reservoir tends to give way at about the center of its side to form a waist. Air bubbles collect below the waist so that they can be discharged along with blood through the outlet tubing while the blood above the waist stagnates there for some time. Another reason is, in a positive sense, to branch the blood stream impinging on the side of the reservoir into an upward stream containing much bubbles and a downward stream containing significantly less bubbles.

According to this invention, a projected portion is previously formed on the blood reservoir in order to prevent the undesired bubble collection and blood stagnation at a waisted portion as stated above.

The preferred configuration of the projected portion 18 of this invention will be described in detail.

As mentioned above, the projected portion 18 takes the role of branching the blood flow into the upward stream containing much bubbles and the downward stream containing significantly less bubbles. It is desirable that an upper ridge 20 extending upward from the crest of the projected portion 18 is shaped so as not to hinder smooth blood flow. Thus the upper ridge 20 may preferably be of a generally straight line as shown in FIG. 1, and most preferably slightly curved so as to be somewhat concave with respect to the blood collecting space as shown in FIG. 7. On the other hand, the downward blood stream flows along a lower ridge 19 extending downward from the crest of the projected portion 18. In consideration of the possibility that a few bubbles can be entrained by this downward blood stream, the lower ridge 19 may preferably be shaped so as to prevent bubbles from settling thereto. This may be attained by forming the lower ridge 19 of a generally straight line as shown in FIG. 1. Most preferably, the lower ridge 19 may be slightly curved so as to be somewhat convex with respect to the blood collecting space as shown in FIG. 7.

The projected portion 18 may be formed partially of the side of reservoir 10 as shown in FIG. 6. Preferably, the projected portion 18 is formed entirely of the side of reservoir 10 by depressing the side into the blood collecting space as shown in FIG. 1.

It is also possible and desirable to form the blood reservoir of the present invention from a pair of rectangular sheets by sealing the edges thereof in such a manner as to produce a triangularly sealed portion at one side, thereby providing a projected portion projecting into the blood collecting space as shown in FIG. 6.

The projected portion 18 of this invention possesses the following specification and functions.

It is assumed in FIG. 1 that the vertical distance of the blood collecting space of the reservoir 10 from its bottom to its top is represented by A and the vertical distance from the bottom of the blood collecting space of the reservoir to the crest of the projected portion 18 is represented by a, while designated at $\alpha$ is the angle between the lower ridge 19 and a perpendicular to the bottom of the reservoir 10. The reservoir 10 of the present invention is preferably designed to be in conformity with the following formulas;

$$0.2 \leq a/A \leq 0.8, \text{ preferably } 0.3 \leq a/A \leq 0.6 \quad (1)$$

$$10° \leq \alpha \leq 45°, \text{ preferably } 20° \leq \alpha \leq 25° \quad (2)$$

Parameters A, a and α are thus limited for the following reason.

If a/A has a value of less than 0.2, the inner wall along the lower ridge of the projected portion is located too near to the port in the blood outlet tubing 13 to avoid the possibility of the inner wall or sheet being sucked along with the blood stream into the blood outlet tubing 13 to clog its port. In addition, the distribution of blood stream changes to increase a clockwise stream generally circulating in the reservoir, permitting air bubbles to enter the blood outlet tubing.

If a/A is more than 0.8, the blood distribution is altered to increase the clockwise circulating blood stream in a region of the reservoir lower than the crest of the projected portion, resulting in debubbling inefficiency and blood stagnation in an upper region of the reservoir.

The lower ridge 19 of the projected portion having an angle α of small than 10° tends to give way to form a waist when the reservoir bulges with blood. Bubbles collect and cling to the lower ridge of the projected portion having an angle α of larger than 45°.

OPERATION

Figure 2:
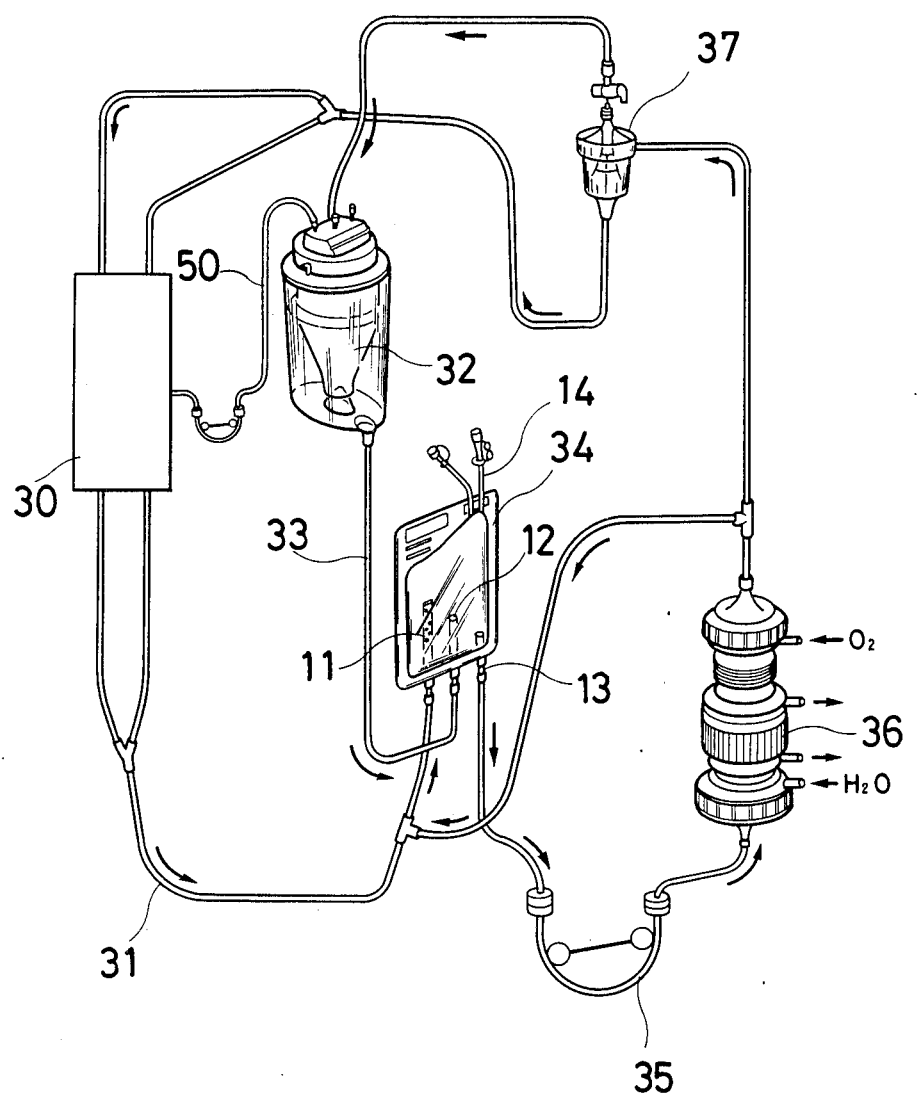
FIG. 2 is a perspective view of a typical oxygenator circuit in which the reservoir is inserted.
Figure 4:
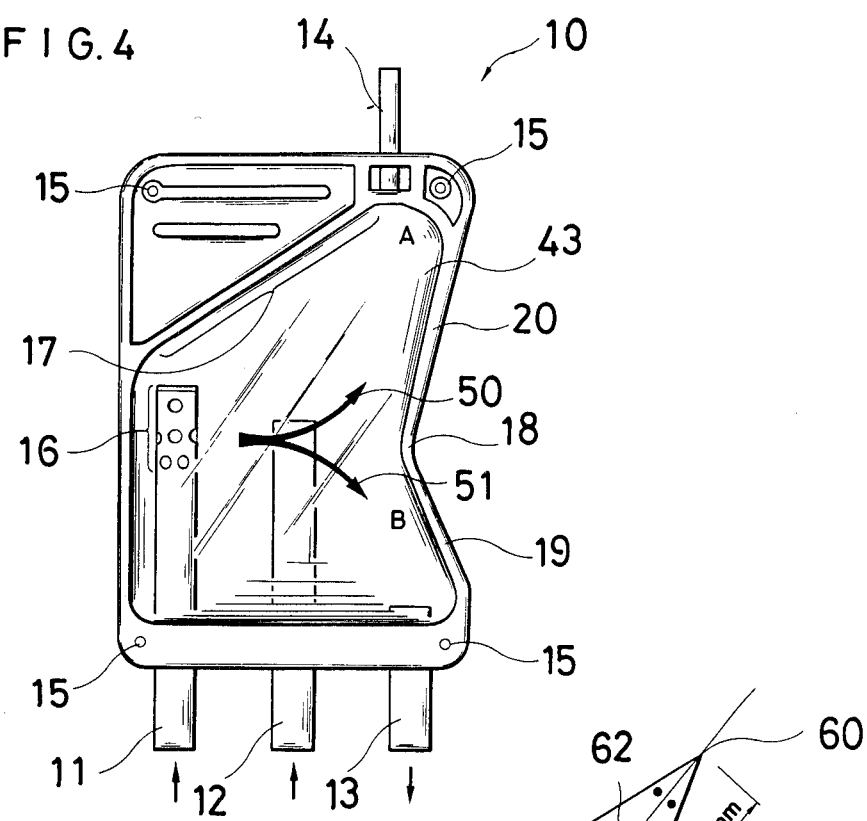
FIG. 4 is an elevation similar to FIG. 1, illustrating blood streams across the projected portion in the reservoir.

An example of an oxygenator circuit is diagrammatically illustrated in FIG. 2.

Blood drained from the patient 30 passes through a drainage line 31 and a blood inlet tubing 11 to a venous reservoir 34. Blood aspirated from the surgical field flows through line 50 into a cardiotomy reservoir 32 for filtration and debubbling, and subsequently passes through a cardiotomy line 33 and a cardiotomy line tubing 12 to the venous reservoir 34. The blood collected in the venous reservoir 34 is debubbled there, with the removed air being exhausted through a vent line tubing 14. The debubbled blood is discharged through a blood outlet tubing 13, pumped by a roller pump 35 into an oxygenator 36 with a heat exchanger where the blood is oxygenated, and then returned to the patient 30 via a bubble trap 37.

If the blood reservoir 34 used in this oxygenator circuit is of a rectangular shape as illustrated in FIG. 2, the reservoir 34 which bulges with blood folds down about the center of its one side to form a waisted portion 40 as shown in FIG. 3.

When the waisted portion 40 is produced at a relatively high level of the side of the reservoir 34, the volume of a downward stream 41 increases as illustrated by a thick arrow in FIG. 3, and a large amount of blood from which bubbles have not been separated enough is undesirably discharged through the blood outlet tubing 13. With the reducing volume of an upward stream 42, blood pools or stagnates in an upper region 43 of the reservoir 34. In contrast, if the waisted portion 40 is formed at a lower level of the side of reservoir 34, blood seldom pools or stagnates in the upper region 43, but the blood at 43 rather flows fast to entrain air bubbles toward the lower region of the reservoir. Moreover, the lower waisted portion 44 having a low angle of inclination causes bubbles 45 to collect and cling thereto. The bubbles 45 clinging to the lower waisted portion 44 do not readily leave or move upward, but are entrained with blood into the blood outlet tubing by the pulsatory motion of the roller pump.

In order to eliminate the disadvantages of such a conventional rectangular reservoir, this invention uses an improved blood reservoir constructed as shown in FIG. 1.

In the blood reservoir of this invention as illustrated in FIG. 1, blood enters the blood collecting space through the ports or openings 16 in the blood inlet tubing 11. While blood flows in a generally horizontal direction, air bubbles which have been mixed in the blood separate and rises to the top. The blood flow then strikes the projected portion 18 provided in one vertical side and is divided into substantially equal blood streams, an upward stream 50 containing much bubbles and a downward stream 51 containing less bubbles.

As described above, the reservoir of this invention has the projected portion 18 which is designed so as to meet the geometrical relationships:

$$0.2 \leq a/A \leq 0.8$$

and $$10° \leq \alpha \leq 45°$$

The volumes of the upward and downward streams 50 and 51 are then substantially equal. Little blood stagnates in the upper region 43 of the blood collecting space. In addition, the lower ridge 19 having an adequate incline and preferably, a gently curved contour allows collecting air bubbles to rise up along the inner wall of the reservoir. Entrainment of bubbles with blood passing through the blood outlet tubing 13 is thus effectively precluded.

EFFECT OF THE INVENTION (1) The reservoir of this invention is provided with the projected portion in one side thereof, that is remoter from the blood inlet tubing and nearer to the blood outlet tubing, by projecting the side edge into the blood collecting space from the vicinity of the intersection between the one side and a horizontal extension of the blood distributing port in the blood inlet tubing. The blood reservoir of the present invention can not only prevent blood pool or stagnation in the upper region of the reservoir even when it is filled up with blood, but also reduce the amount of bubbles clinging to the lower side wall surrounding the lower ridge of the projected portion.

(2) The blood reservoir of this invention is most effective when the projected portion in the reservoir is specifically designed to have the geometrical relationships:

$$0.2 \leq a/A \leq 0.8$$

and $$10° \leq \alpha \leq 45°.$$

EXAMPLE

A blood reservoir as shown in FIG. 1 was formed from a a pair of flexible polyvinyl chloride sheets (S-41, 0.4 mm thickness) by sealing the side edges thereof. The reservoir had a volume of 100 ml and a maximum blood circulating capacity of 800 ml/min. The blood inlet tubing and the cardiotomy line tubing each having a diameter of 6.5 mm were also formed of flexible polyvinyl chloride and projected a distance of 10 cm into the blood collecting space. Ten ports or openings each having a diameter of 3 mm were formed in the end portion of the blood inlet tubing in a symmetrical manner around the tubing.

Several reservoirs were prepared having different projected portions with the dimensions indicated in Table 1. A 35% glycerine solution was circulated through each reservoir at a rate of 800 ml/min. at 25° C. for measurement as described below. The 35% glycerine solution was employed because it had the same viscosity as human blood (Hematocrit 35%, 25 centipoise at 37° C.).

(1) Blood stagnation in the upper region of the blood collecting space

Figure 5:
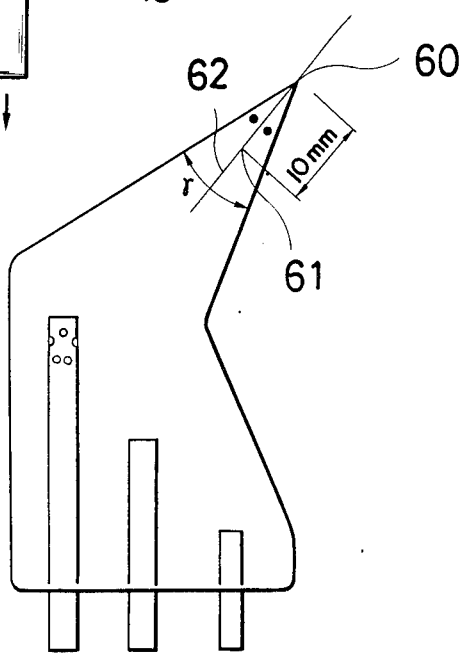
FIG. 5 is a diagrammatic view of the reservoir illustrating how to observe blood stagnation in the reservoir.

In the reservoir diagrammatically shown in FIG. 5, 0.5 ml of black ink was instilled from a sample inlet 60 at the top of the blood collecting space of the reservoir 10 to determine the time for the ink to reach an observation point 61 which is 10 mm away from the sample inlet 60 along the bisector 62 of the included angle γ of the sample inlet 60. The observation point 61 was empirically determined as a measurement point for evaluating the degree of blood stagnation. Ten measurements were averaged to give an average blood stagnation time (second).

(2) Debubbling ability

A bubble trap was connected to the opposite end of the blood outlet tubing to observe whether bubbles were carried with blood into the trap. The results are shown in Table 1 using the following symbols.
O: No bubble was visually observed.
Δ: Very fine bubbles (smaller than 100 μm) were observed.
X: Bubbles larger than 1 mm were observed.

(3) Bubbles clinging to the lower ridge of the projected portion

After priming, the overall reservoir was patted to expel bubbles to an extent normally believed to be necessary and satisfactory. After thirty seconds, the reservoir was observed whether bubbles clinged to the lower ridge 19. The results are shown in Table 1 using the following symbols.
O: No bubble clinged.
Δ: Fine bubbles smaller than 1 mm clinged.
X: bubbles larger than 1 mm clinged.

TABLE 1

| No. | Example I | Example II | Example III | Example IV | Example V | Comparative Example VI |
|---|---|---|---|---|---|---|
| α | 22° | 22° | 20° | 25° | 40° | 0° |
| a/A | 0.4 | 0.5 | 0.6 | 0.3 | 0.4 | 1 |
| Blood stagnation, sec. | 1.1 | 1.3 | 1.8 | 0.8 | 1.2 | — |
| Debubbling ability | O | O | Δ | Δ | O | X |
| Blubbles clinging to the lower ridge of projected portion | O | O | O | O | Δ | O |

What is claimed is:

1. A blood reservoir comprising:
   a hollow container of a flexible synthetic resin defining a space for containing blood therein,
   vent means provided at an upper portion of said container in communication with the space of said container for venting air therefrom,
   blood inlet means and blood outlet means each communicating with the space of said container,
   said blood inlet means including a tubular member extending into the space through a lower portion of said container, a closed top end and a plurality of blood inlet openings formed in a region of the wall of said tubular member below said closed top end, and
   said blood outlet means being located near the lower portion of the space for discharging blood therefrom, and
   a projected portion is provided on one side of the inner surface of said container that is remoter from said blood inlet means and nearer to said blood outlet means, said projected portion being projected into the container space at about the intersection between said one side and the horizontal plane of said blood inlet openings.

2. A blood reservoir according to claim 1 wherein said projected portion is formed entirely in said one side of said inner surface of said container nearer to said blood outlet means by projecting the side into the container space, said projected portion having a crest located in the vicinity of the intersection between said one side of said inner surface of said container and the horizontal plane of said blood inlet openings.

3. A blood reservoir according to claim 2 wherein said one side of said inner surface of said container nearer to said blood outlet means consists of a section extending from said crest to the top of said space and a section extending from said crest to the bottom of said space, each section being a substantially straight line for defining said projected portion.

4. A blood reservoir according to claim 2 wherein the distance A between the top and the bottom of said space and the distance a between said crest and the bottom of said space have the relation:

$$0.2 \leq a/A \leq 0.8.$$

5. A blood reservoir according to claim 1 wherein said container is formed by sealing the side edges of a pair of synthetic resin sheets, said projected portion is provided at the one side of the inner surface of said sealed container, and said tubular member having said plurality of blood inlet openings is provided adjacent the other side of said container.

* * * * *